(12) United States Patent
Han et al.

(10) Patent No.: US 11,759,349 B2
(45) Date of Patent: Sep. 19, 2023

(54) CERAMIC LIFTING AND LOWERING DEVICE FOR THERMOTHERAPEUTIC APPARATUS

(71) Applicant: CERAGEM CO., LTD., Chungcheongnam-do (KR)

(72) Inventors: Sang Cheol Han, Chungcheongnam-do (KR); Seung Gwan Hong, Chungcheongnam-do (KR)

(73) Assignee: CERAGEM CO., LTD., Chungcheongnam-do (KR)

( * ) Notice: Subject to any disclaimer, the term of this patent is extended or adjusted under 35 U.S.C. 154(b) by 1189 days.

(21) Appl. No.: 16/321,894

(22) PCT Filed: Jan. 18, 2018

(86) PCT No.: PCT/KR2018/000854
§ 371 (c)(1),
(2) Date: Jan. 30, 2019

(87) PCT Pub. No.: WO2018/143586
PCT Pub. Date: Aug. 9, 2018

(65) Prior Publication Data
US 2019/0175390 A1 Jun. 13, 2019

(30) Foreign Application Priority Data

Feb. 1, 2017 (KR) .......................... 10-2017-0014567

(51) Int. Cl.
*A61F 7/00* (2006.01)
*A61H 15/00* (2006.01)
(Continued)

(52) U.S. Cl.
CPC ............. *A61F 7/007* (2013.01); *A61H 15/00* (2013.01); *A61H 15/0078* (2013.01);
(Continued)

(58) Field of Classification Search
CPC .... A61H 15/00; A61H 15/02; A61H 15/0078; A61H 39/04; A61H 2201/0142;
(Continued)

(56) References Cited

U.S. PATENT DOCUMENTS 7,118,541 B2 * 10/2006 Kim ........................ A61H 1/00
601/102
2004/0260215 A1 * 12/2004 Kim .................... A61H 15/0078
601/99

(Continued)

FOREIGN PATENT DOCUMENTS

| CL | 201800775 | 8/2018 |
|---|---|---|
| CL | 201901548 | 9/2019 |

(Continued)

OTHER PUBLICATIONS

Office Action issued in Corresponding Chilean Application No. 201902156, dated May 27, 2020 (Spanish).

(Continued)

*Primary Examiner* — Colin W Stuart
*Assistant Examiner* — Douglas Y Sul
(74) *Attorney, Agent, or Firm* — NORTON ROSE FULBRIGHT US LLP

(57) ABSTRACT

To provide a heating apparatus for a heat treatment machine configured to accurately bring each ceramic member into contact with a set moxibustion point, the present invention provides a heating apparatus for a heat treatment machine including a base plate, an ascending and descending member of which one end is coupled to the base plate through a coupler, a plurality of ceramic members provided in the ascending and descending member, a first driving part configured to raise and lower the ascending and descending member, and a second driving part configured to convey the base plate in a horizontal direction.

5 Claims, 9 Drawing Sheets

(51) Int. Cl.
  *A61H 15/02* (2006.01)
  *A61H 39/06* (2006.01)
(52) U.S. Cl.
  CPC ............ *A61H 15/02* (2013.01); *A61H 39/06* (2013.01); *A61H 2015/0021* (2013.01); *A61H 2015/0028* (2013.01); *A61H 2201/0142* (2013.01); *A61H 2201/0146* (2013.01); *A61H 2201/0149* (2013.01); *A61H 2201/0207* (2013.01); *A61H 2201/12* (2013.01); *A61H 2201/1215* (2013.01); *A61H 2201/14* (2013.01); *A61H 2201/1669* (2013.01); *A61H 2201/50* (2013.01); *A61H 2201/5058* (2013.01); *A61H 2201/5082* (2013.01); *A61H 2230/00* (2013.01)
(58) Field of Classification Search
  CPC .... A61H 2201/0146; A61H 2201/0149; A61H 2201/0207; A61H 2201/1669; A61H 2201/50; A61H 2201/5023; A61H 2201/5064; A61H 2230/00; A61H 2205/081; A61F 7/007
  See application file for complete search history.

(56) References Cited

U.S. PATENT DOCUMENTS

| | | | | |
|---|---|---|---|---|
| 2010/0286569 | A1* | 11/2010 | Nagano | A61H 1/008 601/84 |
| 2011/0275968 | A1* | 11/2011 | Liu | A61H 7/007 601/134 |
| 2013/0110007 | A1* | 5/2013 | Jeon | A61B 5/1072 600/594 |
| 2013/0253390 | A1* | 9/2013 | Park | A61H 15/02 601/99 |
| 2014/0371638 | A1* | 12/2014 | Lee | A61H 15/0078 601/18 |

FOREIGN PATENT DOCUMENTS

| | | |
|---|---|---|
| CL | 201902157 | 1/2020 |
| CN | 102464617 | 5/2012 |
| CN | 103860315 | 6/2014 |
| EP | 2638889 | 9/2013 |
| JP | 06125951 | 5/1994 |
| JP | H06125951 | 5/1994 |
| JP | 2004229760 | 8/2004 |
| JP | 3828766 | 10/2006 |
| JP | 2009000278 | 1/2009 |
| KR | 20-0311358 | 4/2003 |
| KR | 10-1181918 | 9/2012 |
| KR | 10-2012-0122420 | 11/2012 |
| KR | 10-2012-0128026 | 11/2012 |
| KR | 10-1528980 | 6/2015 |
| RU | 2005137700 | 6/2006 |
| RU | 106112 | 7/2011 |
| WO | WO 2015/083967 | 6/2015 |
| WO | WO 2016/039563 | 3/2016 |

OTHER PUBLICATIONS

International Search Report and Written Opinion issued in International Patent Application No. PCT/KR2018/000854, dated May 8, 2018.
Extended European Search Report issued in Corresponding European Application No. 18748549.5, dated Oct. 29, 2020.
Office Action issued in Corresponding Chinese Application No. 201710305019.0, dated Oct. 10, 2019 (English Translation provided).
Office Action issued in Corresponding Chinese Application No. 201710305019.0, dated Jun. 8, 2020 (English Translation provided).
Office Action issued in Corresponding Chinese Application No. 201710305019.0, dated Nov. 24, 2020 (No English Translation provided).

* cited by examiner

CERAMIC LIFTING AND LOWERING DEVICE FOR THERMOTHERAPEUTIC APPARATUS

CROSS-REFERENCE TO RELATED APPLICATION

This application is a national phase application under 35 U.S.C. § 371 of International Application No. PCT/KR2018/000854, filed Jan. 18, 2018, which claims priority to and the benefit of Korean Patent Application No. 2017-0014567, filed on Feb. 1, 2017, the disclosures of which are incorporated herein by reference in their entirety.

FIELD OF THE DISCLOSURE

The present invention relates to a heating apparatus for a heat treatment machine, and more particularly, to a heating apparatus for a heat treatment machine configured to accurately bring each ceramic member into contact with a set moxibustion point.

DESCRIPTION OF RELATED ART

A conventional heating apparatus is configured to include a moving space formed to be perpendicular to a body of a moving object which moves laterally along a screw rotated by a motor, a treatment machine moving plate fixedly inserted into the moving space, and when laterally moving, having an engaging protrusion formed on a lower end of a conveying rod configured to vertically move in the moving space, and an ascending and descending spring located between the treatment machine moving plate and the moving object that is configured to vertically move treatment ceramics to apply pressure and heat to an affected part of a user by elongating and contracting along a curve of a human body, and then the treatment ceramics may apply pressure and heat to the affected part at the same intensity by coming into contact with the human body along the curve of the body of the user when the treatment machine moving plate is moved vertically by the ascending and descending spring.

However, since the conventional heating apparatus has a structure in which an entire column of the ceramics ascend and descend by a driving part, and thus an operation range is limited to a vertical direction, the conventional heating apparatus has a limitation in actively coping with a change in a shape of the body when the body has large change, for example, the curve is large, or a sharp change occurs in shape of the body, and accordingly, a massage effect is reduced.

Accordingly, an apparatus capable of relatively actively coping with the change in in the shape of the body to maximize the massage effect has been acutely required.

SUMMARY OF THE INVENTION

The present invention provides a heating apparatus for a heat treatment machine, in which a ceramic member actively responds to a change in a body of a user during a massage process to maximize a massage effect, and product quality is improved to improve consumer satisfaction.

Further, the present invention provides a heating apparatus for a heat treatment machine configured to accurately bring each ceramic member into contact with a set moxibustion point.

To achieve the above-described purpose, the present invention provides a heating apparatus for a heat treatment machine including a base plate, an ascending and descending member of which one end is coupled to the base plate through a coupler, a plurality of ceramic members provided in the ascending and descending member, a first driving part configured to raise and lower the ascending and descending member, and a second driving part configured to convey the base plate in a horizontal direction.

The ascending and descending member may ascend and descend while rotating around the coupler.

The second driving part may convey the base plate in the horizontal direction to unify a location of each of the ceramic members in a vertical direction when the ascending and descending member ascends and descends.

The heating apparatus for a heat treatment machine may further include a controller configured to calculate a conveying distance of the base plate on the basis of an ascending and descending distance of each of the ceramic members and control the second driving part according to the calculated conveying distance.

The first driving part may include a driving part, a rotating member connected to the driving part, and a guide member connected to the ascending and descending member and configured to come into contact with the rotating member.

The rotating member may include a first gear part, and the guide member may include a second gear part having a curved shape and engaged with the first gear part.

The heating apparatus for a heat treatment machine may further include a sensor part configured to sense body information of a user and provide the body information to the controller, and the controller may raise or lower the ascending and descending member according to the sensed body information of the user.

According to the present invention, by an ascending and descending operation of each of first and second ascending and descending members, ceramic members can actively cope with a change in a body of a user during a massage process to maximize a massage effect, and product quality can be improved to improve consumer satisfaction.

Further, according to the present invention, although the first ascending and descending member ascends and descends while rotating around a coupler, since a second driving part conveys a base plate in a horizontal direction, a location of each of the ceramic members can be unified in a vertical direction. Accordingly, each of the ceramic members can come into contact with a set moxibustion point.

DETAILED DESCRIPTION OF THE INVENTION

Figure 1:
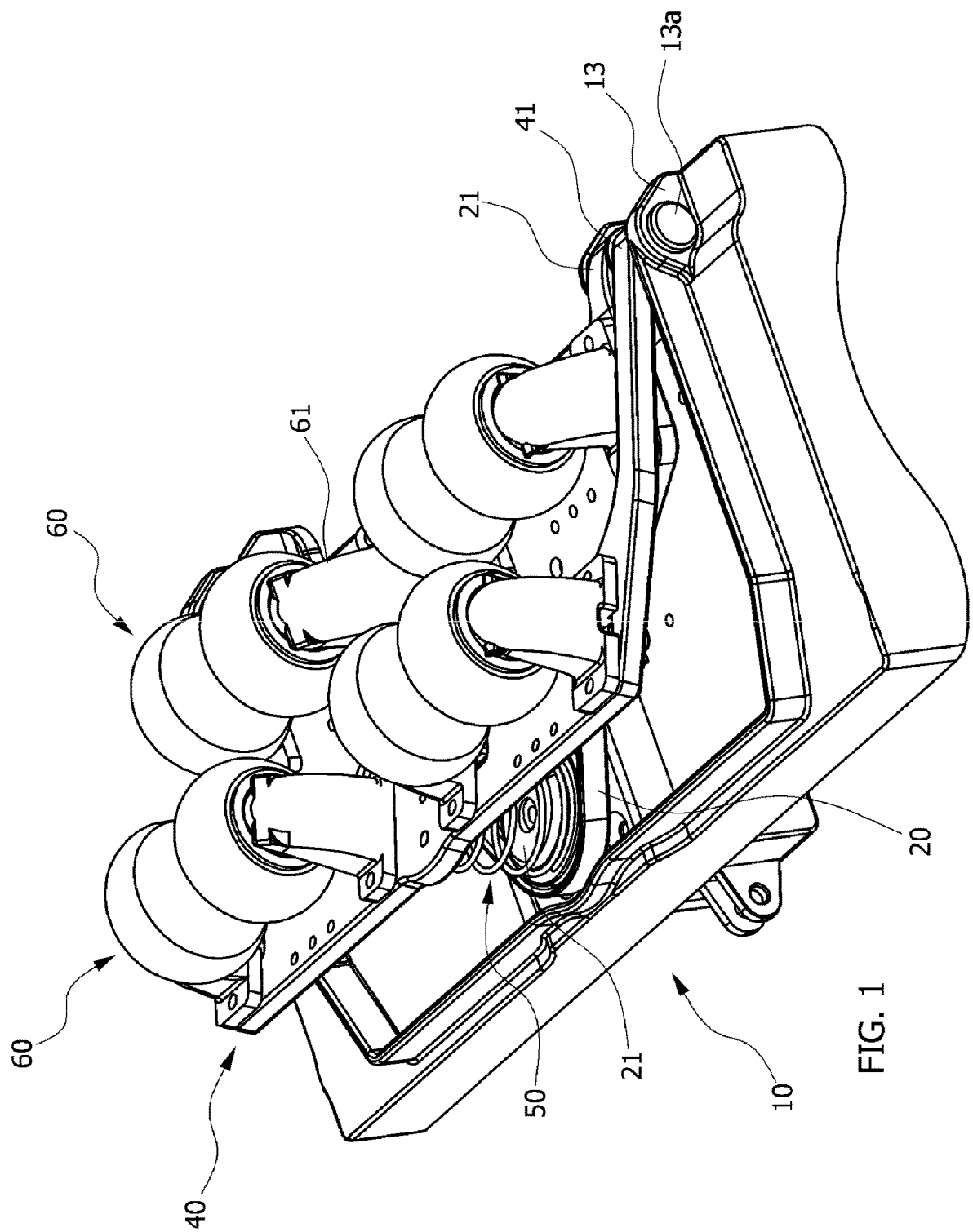
FIG. 1 and FIG. 2 are perspective views of a heating apparatus for a heat treatment machine according to a first embodiment of the present invention.

Hereinafter, exemplary embodiments of the present invention will be described in detail with reference to the accompanying drawings which may allow one of ordinary skill in the art to easily perform the present invention. The present invention may be implemented in various forms and is not limited to the following embodiments. Components not related to the description are omitted in the drawings to clearly describe the present invention, and the same reference symbols are used for the same or similar components in the description.

It should be further understood that the terms "include," "including," "provide," "providing," "have," and/or "having" specify the presence of stated features, integers, steps, operations, elements, components, and/or groups thereof, but do not preclude the presence or addition of one or more other features, integers, steps, operations, elements, components, and/or groups thereof.

Figure 2:
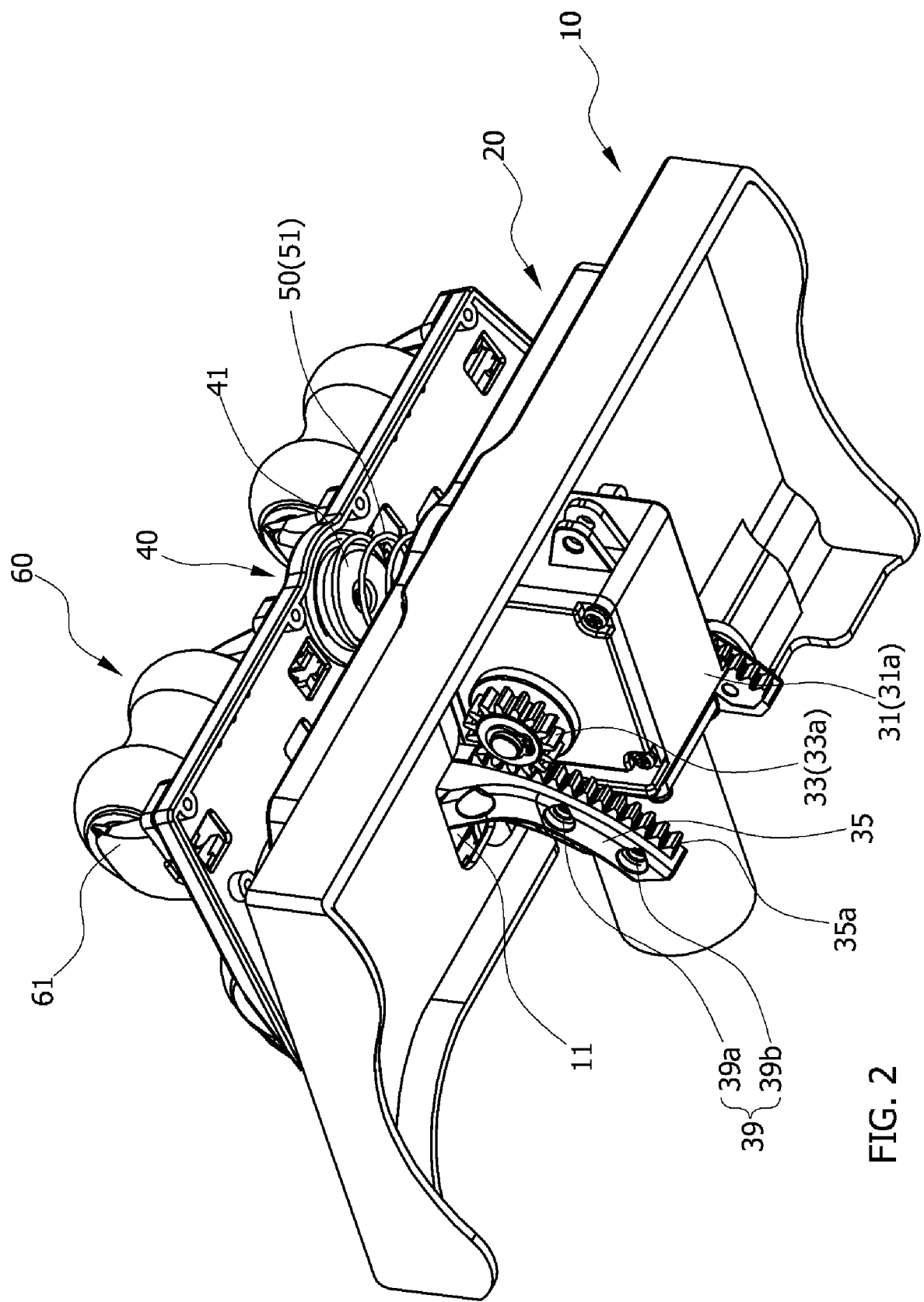
Figure 3:
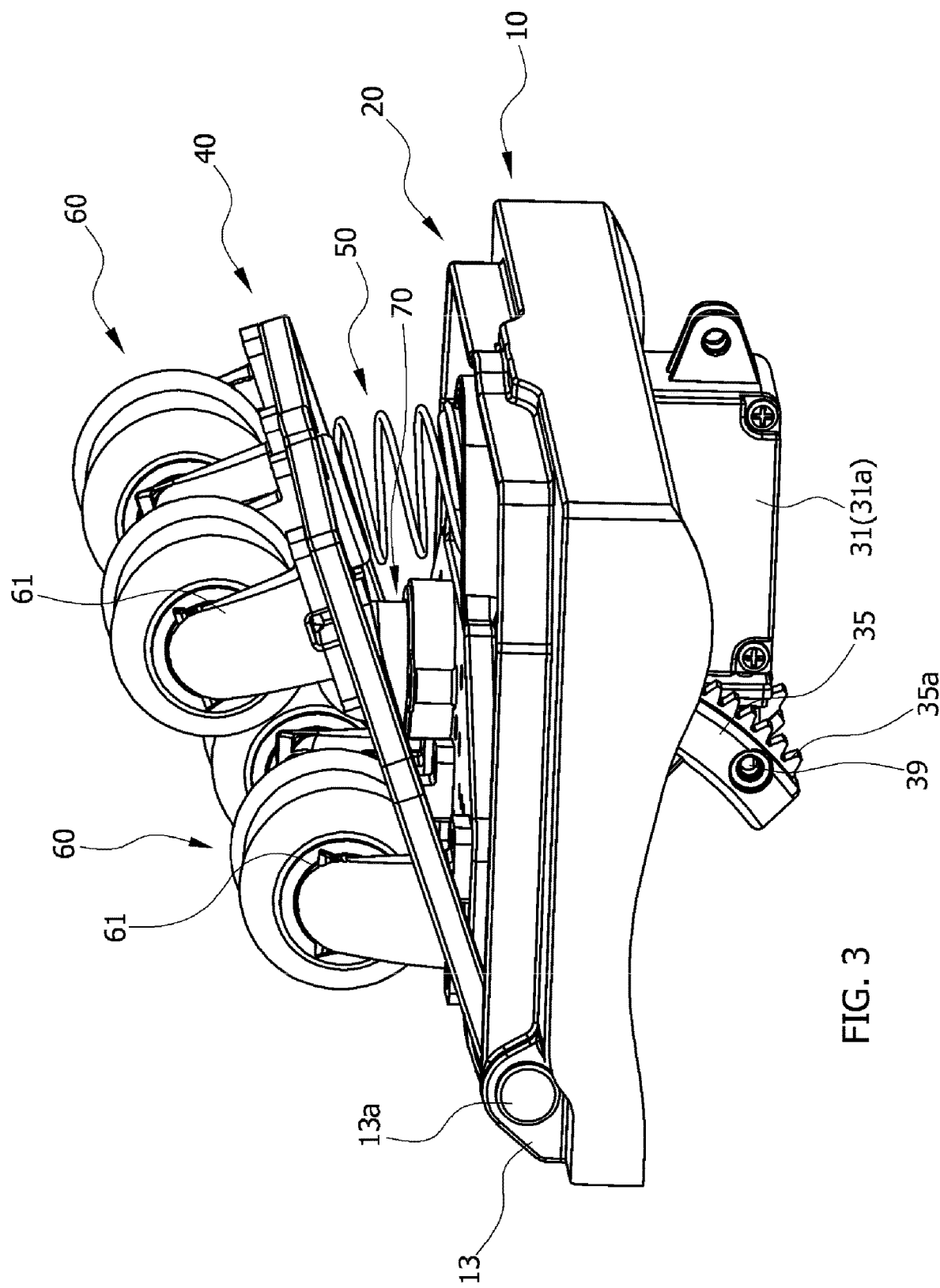
FIG. 3 is a side view of the heating apparatus for a heat treatment machine according to the first embodiment of the present invention.
Figure 4:
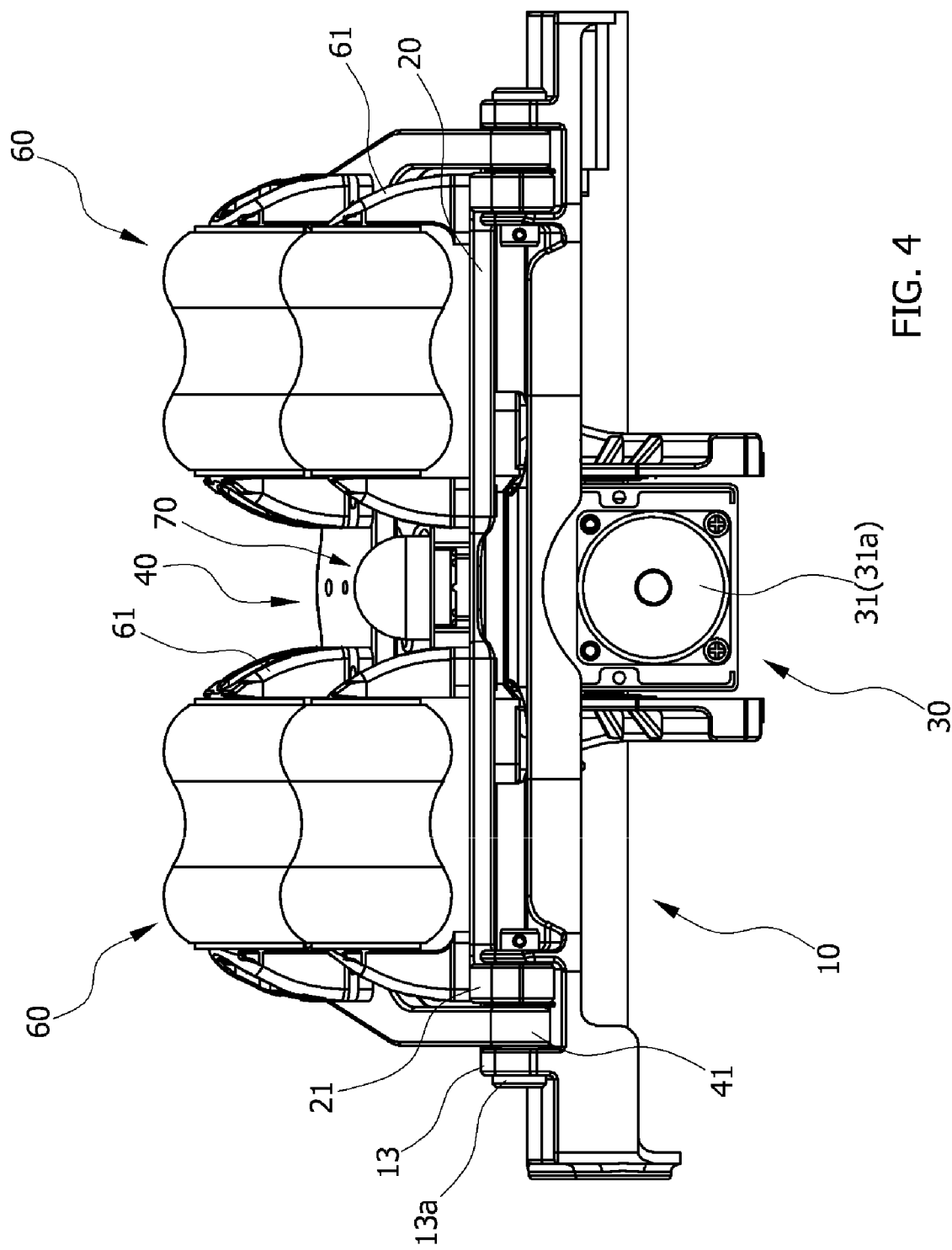
FIG. 4 is a front view of the heating apparatus for a heat treatment machine according to the first embodiment of the present invention.

FIG. 1 and FIG. 2 are perspective views of a heating apparatus for a heat treatment machine according to a first embodiment of the present invention, FIG. 3 is a side view of the heating apparatus for a heat treatment machine according to the first embodiment of the present invention, and FIG. 4 is a front view of the heating apparatus for a heat treatment machine according to the first embodiment of the present invention.

Meanwhile, the heating apparatus for a heat treatment machine according to the first embodiment of the present invention may be installed in heat treatment machines having various types such as a bed type, a chair type, etc.

As shown in FIGS. 1 to 4, the heating apparatus for a heat treatment machine according to the first embodiment of the present invention may include a base plate 10, a first ascending and descending member 20, a second ascending and descending member 40, a first driving part 30, an elastic member 50, and ceramic members 60.

Here, a conveying part (not shown) is provided at one side of the base plate 10, and the ceramic members 60 are moved by the conveying part and come into contact with a part of the body of a user to perform a massage function and a moxibustion function through heat supply.

To further describe the conveying part, guide protrusions (not shown) provided at both sides of the base plate 10 may be connected to a guide rail (not shown) formed in a main body of the heat treatment machine, a fixing bracket (not shown) may be mounted on one side of the base plate 10, and a conveying motor (not shown) may be connected to the fixing bracket.

Since a first conveying gear (not shown) is provided at an end portion of a driving shaft of the conveying motor, and a second conveying gear (not shown) engaged with the first conveying gear (not shown) is provided at the main body of the heat treatment machine, the heating apparatus according to the embodiment of the present invention may be conveyed in a frontward direction or a rearward direction.

The base plate 10 may be formed as a plate having a quadrangular shape, and includes a pair of hinge couplers 13 configured to upwardly protrude at a front thereof, and the first ascending and descending member 20 and the second ascending and descending member 40 are provided with a first corresponding hinge coupler (not shown) and a second corresponding hinge coupler (not shown) at front ends thereof, respectively, to correspond to the hinge couplers 13. Further, the hinge couplers 13, the first corresponding hinge coupler (not shown), and the second corresponding hinge coupler (not shown) are coupled by coupling pins 13a.

Accordingly, the first ascending and descending member 20 and the second ascending and descending member 40 may ascend and descend while rotating around the hinge couplers 13, that is, the coupling pins 13a.

Although the first ascending and descending member 20 may be formed as a plate shape, and a shape thereof is preferable to have a roughly triangular shape, the first ascending and descending member 20 may be formed in various shapes according to necessity.

The plurality of ceramic members 60 rotatably connected to support brackets 61 are provided on an upper surface of the first ascending and descending member 20, and although the pair of ceramic members 60 may be provided as shown in FIG. 1, an exemplary massage function may be realized by increasing or decreasing the number of ceramic members 60.

The first driving part 30 may include a driving part 31 configured to raise and lower the first ascending and descending member 20 and mounted on the base plate 10, a rotating member 33 connected to the driving part 31, and a guide member 35 connected to the first ascending and descending member 20 and configured to come into contact with the rotating member 33.

Here, the driving part 31 may include a gear box 31a mounted on a lower surface of the base plate 10, and the rotating member 33 is connected to both sides of the gear box 31a and driven by the driving part 31 to rotate.

Further, the guide member 35 is provided under the first ascending and descending member 20, comes into contact with the rotating member 33, and ascends and descends through a guide hole 11 formed in the base plate 10 when the rotating member 33 rotates, and the first ascending and descending member 20 connected to the rotating member 33 also ascends and descends.

In this case, the guide member 35 is formed in a gradually curved shape and comes into contact with the rotating member 33 having a disc shape to receive power.

Specifically, as shown in FIG. 2, the rotating member 33 may include a first gear part 33a, and the guide member 35 may include a second gear part 35a having a curved shape and engaged with the first gear part 33a of the rotating member 33.

Accordingly, when the first gear part 33a of the rotating member 33 is rotated by the driving part 31, the second gear part 35a of the guide member 35 ascends and descends through the guide hole 11 along the first gear part 33a, and the first ascending and descending member 20 connected to the guide member 35 also ascends and descends.

An engagement part 39 may be provided so that the guide member 35 and the second gear part 35a may be coupled to and separated from each other.

For example, the engagement part 39 may engage and separate the guide member 35 and the second gear part 35a through a bolt engaging method so that the guide member 35 and the second gear part 35a may be attachable to and detachable from each other.

In this case, a coupling hole 39a may be formed in each of the guide member 35 and the second gear part 35a so that the guide member 35 and the second gear part 35a correspond to each other, and the guide member 35 and the second gear part 35a may be fixed by inserting and fastening a coupling bolt 39b into the coupling hole 39a.

Accordingly, when the second gear part 35a needs to be replaced or repaired due to abrasion or damage, since the coupling bolt 39b may be released to be separated and then reassembled, a maintenance process may be simply performed.

Unlike the first ascending and descending member 20, the second ascending and descending member 40 ascends and descends without power supply according to a curve or shape of the body with which the ceramic members 60 come into contact.

To this end, the elastic member 50 uses elasticity thereof for an ascending and descending operation of the second ascending and descending member 40.

The elastic member 50 elastically supports the second ascending and descending member 40 and connects the base plate 10 and the second ascending and descending member 40, or the first ascending and descending member 20 and the second ascending and descending member 40.

That is, as an elastic spring 51, the elastic member 50 implements the ascending and descending operation of the second ascending and descending member 40 by having each end portion connected to an upper surface of the first ascending and descending member 20 and a lower surface of the second ascending and descending member 40, or an upper surface of the base plate 10 and the lower surface of the second ascending and descending member 40.

In this case, a first insertion part 21 and a second insertion part 41 may be provided to be corresponding to each other on the base plate 10 or in the first ascending and descending member 20 and the second ascending and descending member 40 so that each end portion of the elastic spring 51 is insertion-fixed, and in this case, each of the insertion parts 21 and 41 may be manufactured in a protrusion shape or formed in a groove shape so that each end portion of the elastic spring 51 may be forcibly inserted into the insertion parts 21 and 41 to be insertion-fixed.

The ceramic members 60 are rotatably provided on each of the first ascending and descending member 20 and the second ascending and descending member 40, and a heat member is provided in each of the ceramic members 60 to perform a heat massage function and a moxibustion function.

Further, the ceramic members 60 are each rotatably connected to the support brackets 61 connected to an upper surface of each of the first ascending and descending member 20 and the second ascending and descending member 40, and are raised and lowered by the ascending and descending members 20 and 40 according to the curve of the body to perform a massage process and a moxibustion process when coming into contact with the body of the user.

In this case, the first ascending and descending member 20 may adjust a massage pressure, and the second ascending and descending member 40 may improve adherence to the body of the user.

Meanwhile, the plurality of ceramic members 60 are provided on each of the first ascending and descending member 20 and the second ascending and descending member 40, so as to be capable of improving balance and stability while securing a sufficient operation area when coming into contact with the body.

Figure 5:
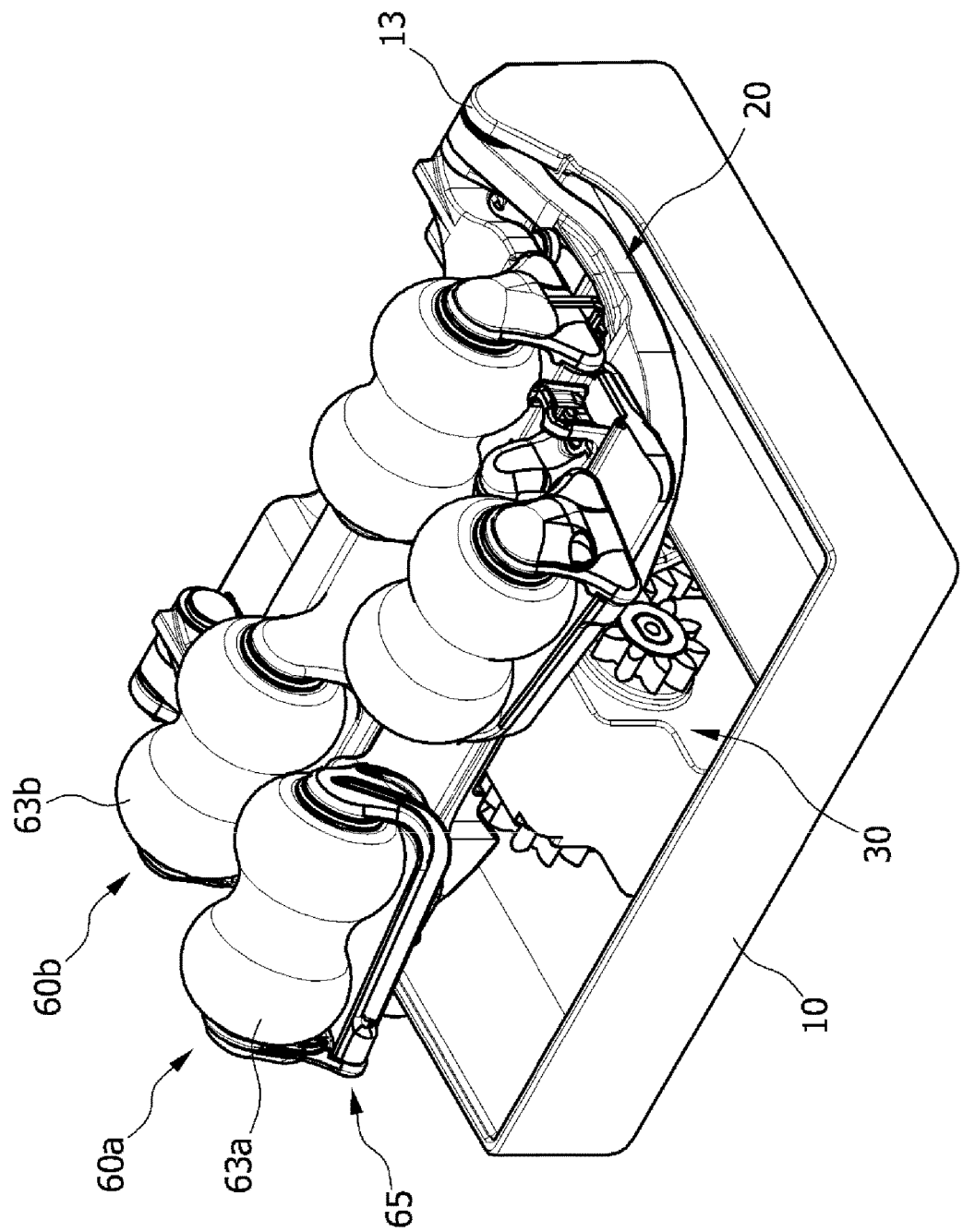
FIG. 5 is a perspective view of a heating apparatus for a heat treatment machine according to a second embodiment of the present invention.
Figure 6:
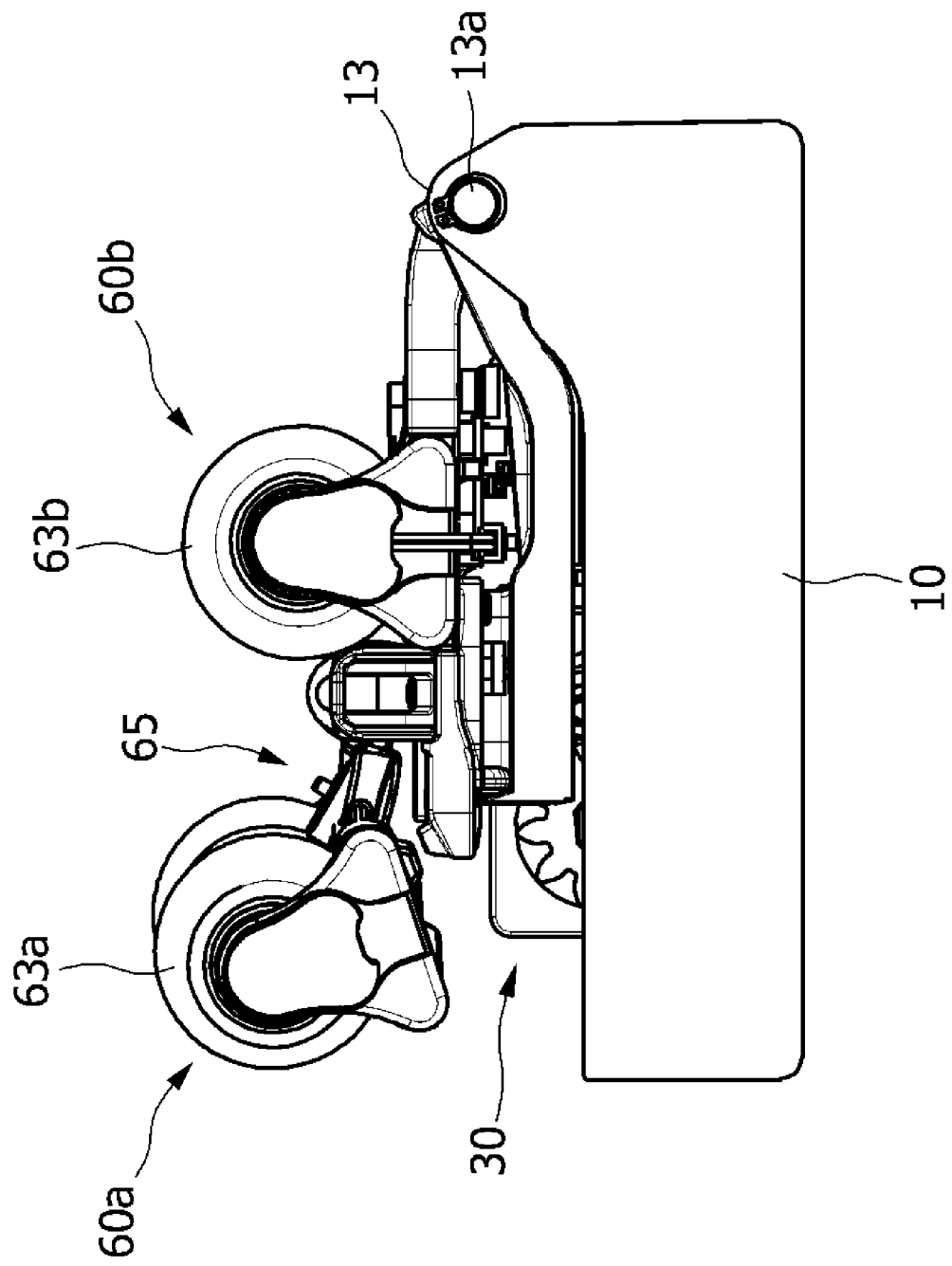
FIG. 6 is a side view of the heating apparatus for a heat treatment machine according to the second embodiment of the present invention.

FIG. 5 is a perspective view of a heating apparatus for a heat treatment machine according to a second embodiment of the present invention. Further, FIG. 6 is a side view of the heating apparatus for a heat treatment machine according to the second embodiment of the present invention.

Meanwhile, components of the heat treatment machine according to the second embodiment of the present invention the same as those of the first embodiment of the present invention have identical reference numerals.

Hereinafter, the heating apparatus for a heat treatment machine according to the second embodiment of the present invention will be described with reference to FIGS. 5 and 6, but descriptions of the components the same as those of the above-described first embodiment of the present invention will be omitted.

The heat treatment machine according to the second embodiment of the present invention may include a base plate 10, an ascending and descending member 20, a first driving part 30, first ceramic members 60a, second ceramic members 60b, and ceramic driving parts 65.

Here, a pair of hinge couplers 13 configured to protrude upwardly are provided on one end of the base plate 10, corresponding hinge couplers (not shown) are each provided on one ends of the ascending and descending member 20 to correspond to the hinge couplers 13. Further, the hinge couplers 13 and the corresponding hinge couplers (not shown) may be coupled to each other by coupling pins 13a.

Accordingly, the ascending and descending member 20 may ascend and descend while rotating around the hinge couplers 13, that is, the coupling pins 13a.

In this case, when the first driving part 30 raises and lowers the ascending and descending member 20, the ascending and descending member 20 ascends and descends while rotating around the hinge couplers 13.

The first ceramic members 60a and the second ceramic members 60b are each rotatably provided on the ascending and descending member 20 and a heat member is provided in each of the ceramic members 60a and 60b to perform a heat massage function and a moxibustion function.

The first ceramic members 60a may have at least a pair of first thermal ceramics 63a.

Here, the pair of first thermal ceramics 63a may be located to be spaced apart from each other at a predetermined distance and raised and lowered when the first driving part 30 raises and lowers the ascending and descending member 20. Further, the first thermal ceramics 63a may be raised and lowered by the ceramic driving parts 65 which will be described below.

The ceramic driving parts 65 may vary a gap between the pair of first thermal ceramics 63a according to an ascending and descending location thereof. For example, a gap between the pair of first thermal ceramics 63a at a first location may be greater than a gap between the pair of first thermal ceramics 63a at a second location.

Further, the ceramic driving parts 65 may move the first ceramic members 60a so that the gap between the pair of first thermal ceramics 63a gradually decreases when the first ceramic members 60a move from the first location to the second location.

As described above, since the gap between the first thermal ceramics 63a is provided to vary according to the ascending and descending location of the first thermal ceramics 63a, the first thermal ceramics 63a may come into contact with a body part according to a width of the body part. For example, in body parts, since the cervical vertebrae has a width smaller than a back, all of the pair of first thermal ceramics 63a may come into contact with the cervical vertebrae by decreasing the gap between the first thermal ceramics 63a when massaging the cervical vertebrae.

Accordingly, by adjusting the gap between the first thermal ceramics 63a, a massage effect and a heat treatment effect may be maximized.

The second ceramic members 60b may be located behind the first ceramic member 60a and may have at least a pair of second thermal ceramics 63b.

Here, the pair of second thermal ceramics 63b may be located to be spaced apart from each other at a predetermined distance and raised and lowered when the first driving part 30 raises and lowers the ascending and descending member 20.

The heating apparatus for a heat treatment machine according to the second embodiment of the present invention may move the first thermal ceramics 63a and the second thermal ceramics 63b in a vertical direction by driving the first driving part 30 and the ceramic driving parts 65 while being moved in a horizontal direction by the conveying part (not shown).

That is, when the ascending and descending member 20 is raised and lowered by the first driving part 30, the first thermal ceramics 63a and the second thermal ceramics 63b may also be raised and lowered, and in addition, the first thermal ceramics 63a and the second thermal ceramics 63b may also be raised and lowered by the ceramic driving parts 65.

Accordingly, the heating apparatus for a heat treatment machine according to the second embodiment of the present invention may perform a massage or heat treatment to the cervical vertebrae and the back by adjusting the gap between the pair of first thermal ceramics 63a. Further, the heating apparatus may maximize the massage effect and the heat treatment effect by providing uniform massage intensity for each body part.

Figure 7:
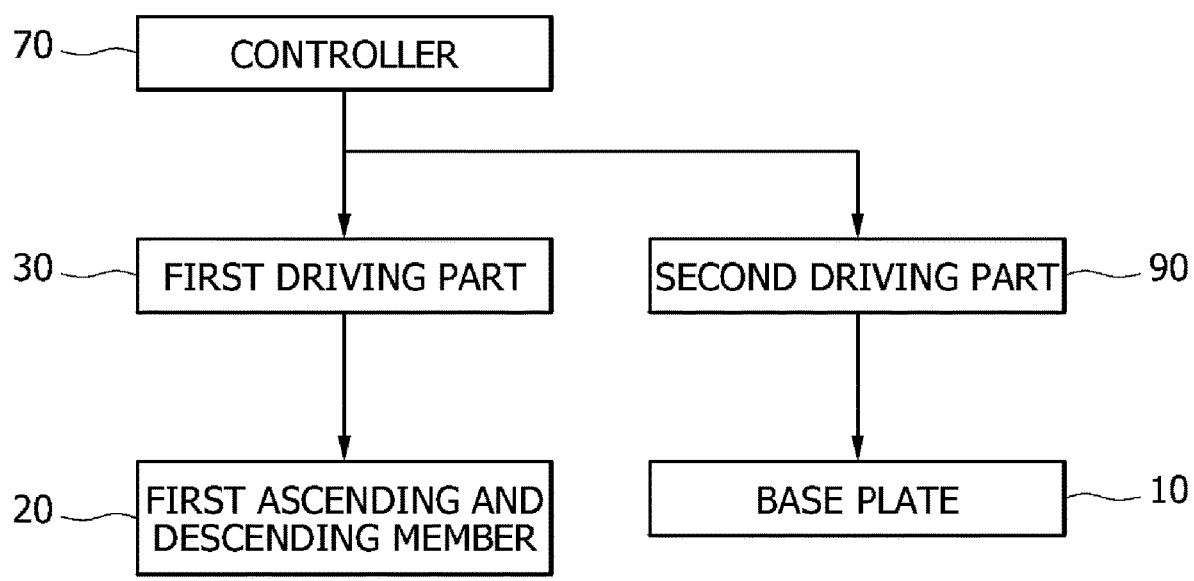
FIG. 7 is a block diagram of a heating apparatus for a heat treatment machine according to one embodiment of the present invention.
Figure 8:
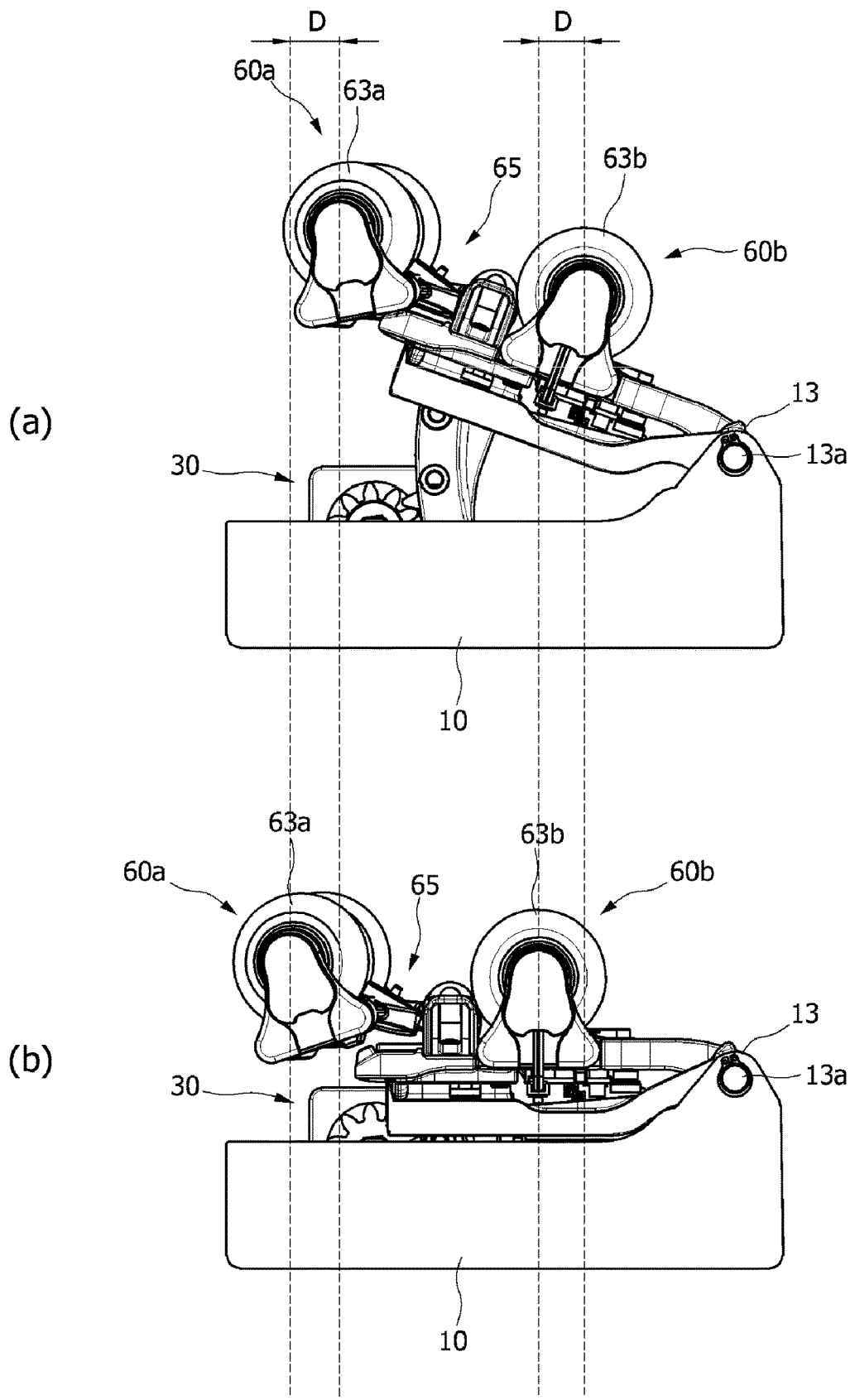
FIG. 8 is a view for describing an operation state of the heating apparatus for a heat treatment machine when a second driving part is not provided in FIG. 7.
Figure 9:
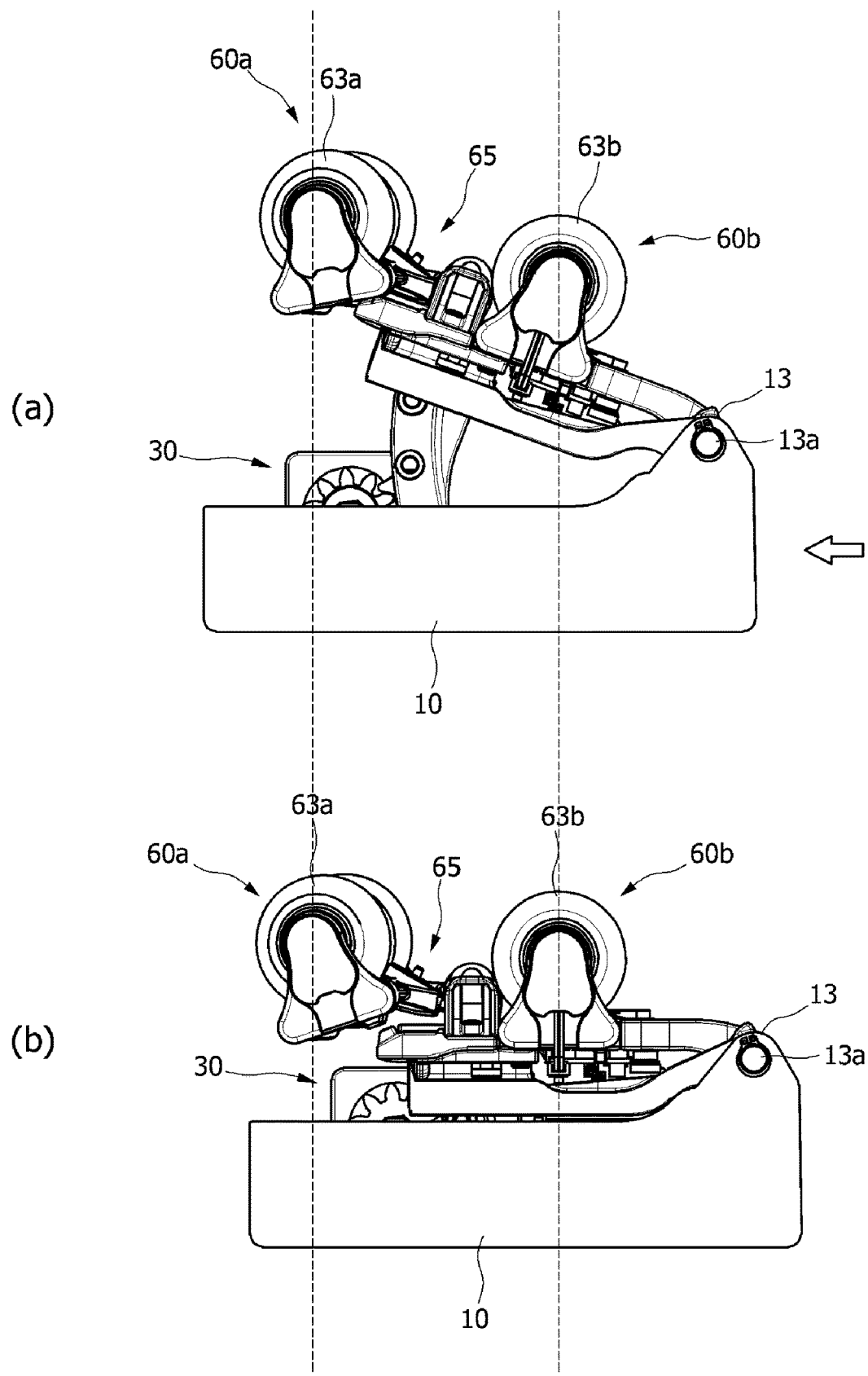
FIG. 9 is a view for describing an operation state of the heating apparatus for a heat treatment machine when the second driving part is provided in FIG. 7.

FIG. 7 is a block diagram of a heating apparatus for a heat treatment machine according to one embodiment of the present invention, FIG. 8 is a view for describing an operation state of the heating apparatus for a heat treatment machine when the second driving part is not provided in FIG. 7, and FIG. 9 is a view for describing an operation state of the heating apparatus for a heat treatment machine when the second driving part is provided in FIG. 7.

As shown in FIG. 7, the heating apparatus for a heat treatment machine according to the embodiment of the present invention may include a controller 70, a first driving part 30, and a second driving part 90.

A sensor part (not shown) such as a sensor or scanner is provided in a heat treatment machine, which includes the heating apparatus for a heat treatment machine according to the embodiment of the present invention, to sense body information of a user and then provide the body information to the controller 70 during a massage process.

Further, since the controller 70 raises and lowers a first ascending and descending member 20 by driving the first driving part 30 according to the body information of the user, both ceramic members 60 may smoothly come into contact with a body.

In this case, a second ascending and descending member 40 ascends and descends by itself due to an elastic member 50 according to a change of the body of the user so that the ceramic members 60 may smoothly come into contact with the body and thus a massage effect may maximally exhibited.

Meanwhile, as shown in FIG. 8, in a case in which the second driving part 90 is not provided in the heating apparatus for a heat treatment machine according to the embodiment of the present invention, when the first ascending and descending member 20 ascends and descends while rotating around couplers 13 and 45, a location of each of the ceramic members 60 is changed in a vertical direction. That is, in a case in which first ascending and descending member 20 ascends, as in FIG. 9 (a), and in a case in which first ascending and descending member 20 descends, as in FIG. 9 (b), the location of each of the ceramic members 60 moves in a horizontal direction in a horizontal distance D.

As described above, when the first ascending and descending member 20 ascends and descends and the location of each of the ceramic members 60 moves in the horizontal direction, a moxibustion point is changed while performing a moxibustion process. That is, in a descending state of the first ascending and descending member 20, when the controller 70 sets the moxibustion point according to the body information of the user sensed by the sensor part, and then the first ascending and descending member 20 ascends, each of the ceramic members 60 departs from the set moxibustion point and comes into contact with another body part.

Here, the heating apparatus for a heat treatment machine according to the embodiment of the present invention prevents a change of the moxibustion point while performing the moxibustion process through the second driving part 90.

Specifically, the second driving part 90 conveys the base plate 10 in a horizontal direction and unifies the location of each of the ceramic members 60 in a vertical direction when the first ascending and descending member 20 ascends and descends.

In this case, the controller 70 calculates a conveying distance of the base plate 10 on the basis of an ascending and descending distance of each of the ceramic members 60 and controls the second driving part 90 according to the calculated conveying distance.

For example, as shown in FIG. 9, when the first ascending and descending member 20 ascends, as in FIG. 9 (a), from a state of descending, as in FIG. 9 (b), although the first ascending and descending member 20 ascends and descends while rotating around the couplers 13 and 45, since the second driving part 90 conveys the base plate 10 in the horizontal direction, the location of each of the ceramic members 60 may be unified in a vertical direction.

That is, when the first ascending and descending member 20 ascends, as in FIG. 9 (a), from the state of descending, as in FIG. 9 (b), since the second driving part 90 conveys the base plate 10 to a right side in the horizontal distance D (see FIG. 8), the location of each of the ceramic members 60 may be unified in a vertical direction.

Accordingly, each of the ceramic members 60 may accurately come into contact with the set moxibustion point.

Although one embodiment of the present invention is described above, the spirit of the present invention is not limited to the embodiment shown in the description, and although those skilled in the art may provide other embodiments due to addition, change, or removal of the components within the scope of the same spirit of the present invention, such embodiments and the above embodiments are also included in the scope of the spirit of the present invention.

REFERENCE NUMERALS

10: base plate
20: first ascending and descending member
30: first driving part
40: second ascending and descending member
50: elastic member 60: ceramic member
70: controller
90: second driving part

The invention claimed is:

1. A heating apparatus for a heat treatment machine, comprising:
   a base plate;
   an ascending and descending member of which one end is coupled to the base plate through a coupler and coupling pins, wherein the ascending and descending member is configured to ascend and descend by rotating around the coupling pins;
   a plurality of ceramic members each having a heating member and each provided in the ascending and descending member;
   a first driving part coupled to the ascending and descending member and configured to raise and lower the ascending and descending member;
   a second driving part coupled to the base plate and configured to convey the base plate in a horizontal direction; and
   a controller configured to calculate a conveying distance of the base plate on the basis of an ascending and descending distance of each of the ceramic members, and control the second driving part according to the calculated conveying distance, wherein the second driving part is configured to convey the base plate in the horizontal direction to unify a location of each of the ceramic members before and after the ascending and descending member is raised in a vertical direction when a vertical position of each of the ceramic members is shifted while the ascending and descending member ascends and descends.

2. The heating apparatus for a heat treatment machine of claim 1, wherein the first driving part includes:
   a driving part;
   a rotating member connected to the driving part; and a guide member connected to the ascending and descending member and configured to come into contact with the rotating member.

3. The heating apparatus for a heat treatment machine of claim 2, wherein: the rotating member includes a first gear part; and the guide member includes a second gear part having a curved shape and engaged with the first gear part.

4. The heating apparatus for a heat treatment machine of claim 1, further comprising a sensor part configured to sense body information of a user and provide the body information to the controller.

5. The heating apparatus for a heat treatment machine of claim 4, wherein the controller raises and lowers the ascending and descending member according to the sensed body information of the user.

* * * * *